(12) United States Patent
Ueda

(10) Patent No.: US 8,794,443 B2
(45) Date of Patent: Aug. 5, 2014

(54) INDIVIDUALLY PACKAGED PRODUCT

(75) Inventor: Takahiro Ueda, Kanonji (JP)

(73) Assignee: Unicharm Corporation, Shikokuchuo-shi (JP)

( * ) Notice: Subject to any disclaimer, the term of this patent is extended or adjusted under 35 U.S.C. 154(b) by 140 days.

(21) Appl. No.: 13/389,211

(22) PCT Filed: Jul. 29, 2010

(86) PCT No.: PCT/JP2010/063228
§ 371 (c)(1),
(2), (4) Date: Feb. 6, 2012

(87) PCT Pub. No.: WO2011/016502
PCT Pub. Date: Feb. 10, 2011

(65) Prior Publication Data
US 2012/0132551 A1 May 31, 2012

(30) Foreign Application Priority Data
Aug. 6, 2009 (JP) ................................ 2009-183388

(51) Int. Cl.
| B65D 69/00 | (2006.01) |
| A61B 17/06 | (2006.01) |
| A61F 13/551 | (2006.01) |
| A61F 13/84 | (2006.01) |
| A61F 13/472 | (2006.01) |

(52) U.S. Cl.
CPC ............. *A61F 13/5514* (2013.01); *A61F 13/84* (2013.01); *A61F 13/472* (2013.01)
USPC ....... 206/581; 206/440; 206/460; 604/385.06

(58) Field of Classification Search
CPC .... A61F 13/84; A61F 13/472; A61F 13/5514
USPC ................. 206/438, 440, 441, 460, 494, 581; 604/385.02–385.06
See application file for complete search history.

(56) References Cited

U.S. PATENT DOCUMENTS

| 3,095,088 A | 6/1963 | Blaikie et al. |
| 4,738,678 A | 4/1988 | Paulis |

(Continued)

FOREIGN PATENT DOCUMENTS

| JP | 54-7599 | 1/1979 |
| JP | 7-506034 | 7/1995 |

(Continued)

OTHER PUBLICATIONS

Extended European Search Report dated May 17, 2013, directed to EP Application No. 10806501.2; 5 pages.

(Continued)

*Primary Examiner* — Luan K Bui
(74) *Attorney, Agent, or Firm* — Morrison & Foerster LLP

(57) ABSTRACT

[PURPOSE]
To provide an individually packaged product that is resistant to contaminants infiltration and can be hygienically transported.
[SOLUTION MEANS]
An individually packaged product comprising a first individual package formed by covering an absorbent article with a packaging sheet, and a second individual package, wherein the packaging sheet has a middle region and a first region and second region located on either side of the middle region, the second region is folded onto the middle region sandwiching the absorbent article therebetween, and the first region being folded onto part of the second region, while the first region is anchored to the outer face of the second region, and the second individual package is situated on the first region and second region and anchored to at least part of the outer face of the first region.

8 Claims, 8 Drawing Sheets

(56) References Cited

U.S. PATENT DOCUMENTS

| | | | |
|---|---|---|---|
| 5,460,622 A | 10/1995 | Dragoo et al. | |
| 5,484,636 A * | 1/1996 | Berg et al. | 206/440 |
| 5,569,228 A * | 10/1996 | Byrd et al. | 604/385.02 |
| 5,569,230 A * | 10/1996 | Fisher et al. | 604/385.06 |
| 5,683,377 A * | 11/1997 | Mizutani | 206/438 |
| 5,792,131 A | 8/1998 | Mizutani | |
| 6,911,022 B2 * | 6/2005 | Steger et al. | 604/385.05 |
| 2002/0013564 A1 | 1/2002 | Kubalek et al. | |
| 2002/0156448 A1 | 10/2002 | Steger et al. | |
| 2003/0102239 A1 * | 6/2003 | Beard | 206/440 |
| 2003/0114823 A1 * | 6/2003 | Bosselaar et al. | 604/385.06 |
| 2004/0226843 A1 | 11/2004 | Hermansson et al. | |
| 2007/0142810 A1 * | 6/2007 | Visscher | 604/385.06 |
| 2007/0142811 A1 | 6/2007 | Lais | |
| 2008/0269710 A1 | 10/2008 | Caracci et al. | |

FOREIGN PATENT DOCUMENTS

| | | |
|---|---|---|
| JP | 3532199 | 7/1995 |
| JP | 9-10257 | 1/1997 |
| JP | 9-10258 | 1/1997 |
| JP | 4191596 | 10/2004 |
| JP | 2009-518248 | 5/2009 |
| WO | WO-93/21878 | 11/1993 |

OTHER PUBLICATIONS

International Search Report mailed Sep. 14, 2010, directed to counterpart International Application No. PCT/JP2010/063228; 4 pages.

* cited by examiner

Fig. 2
(a)
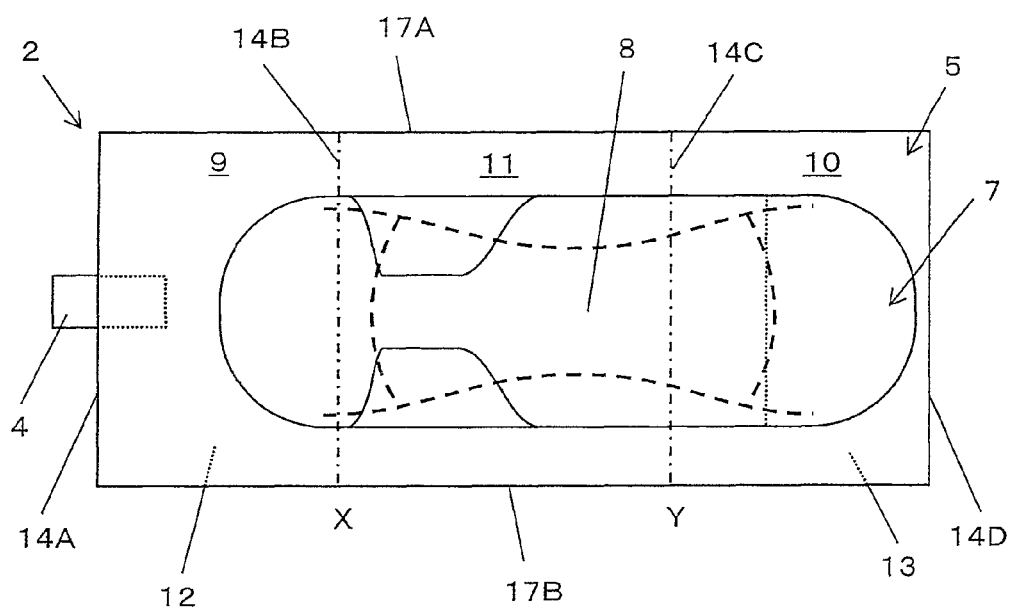
(b)
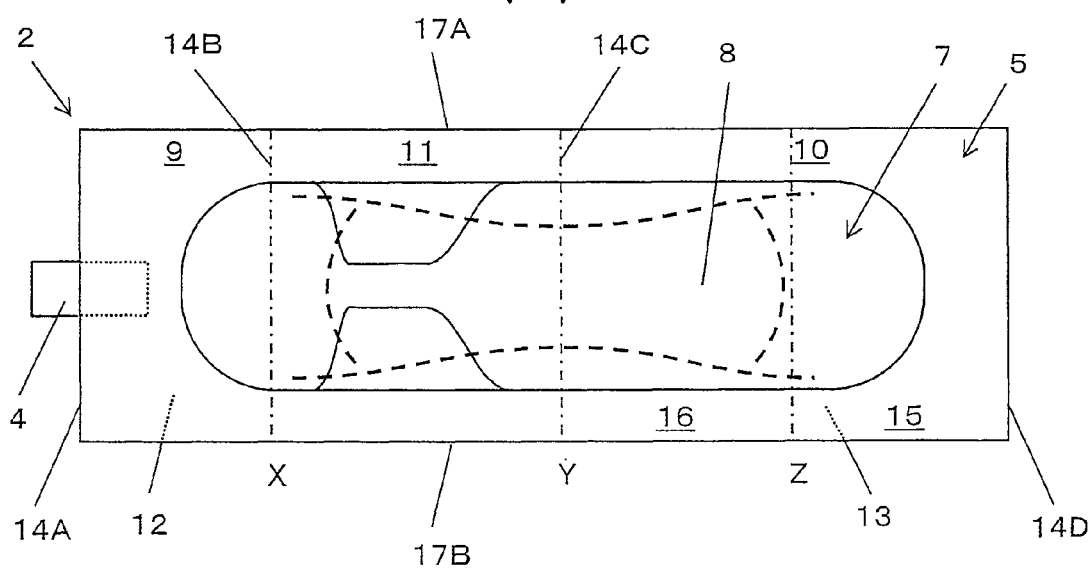

Fig.3
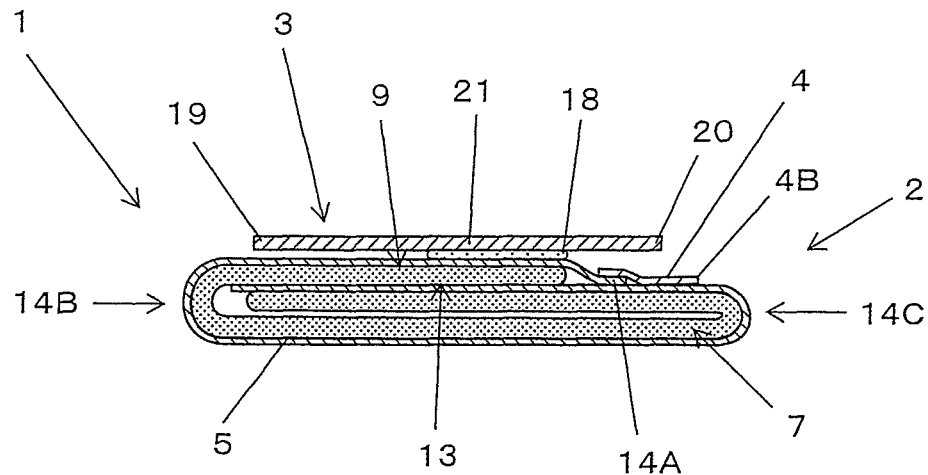
Fig.4
(a)
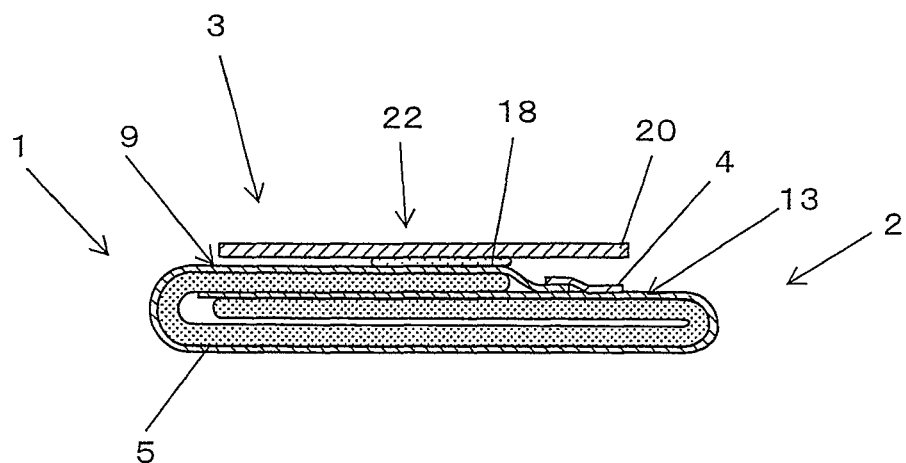
(b)
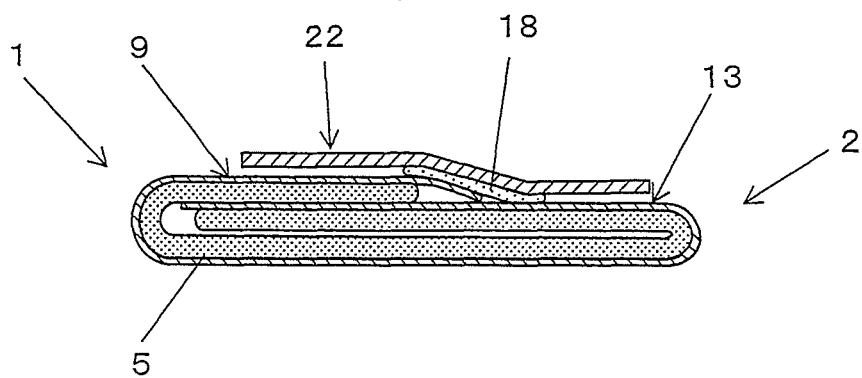

Fig.8
(a)
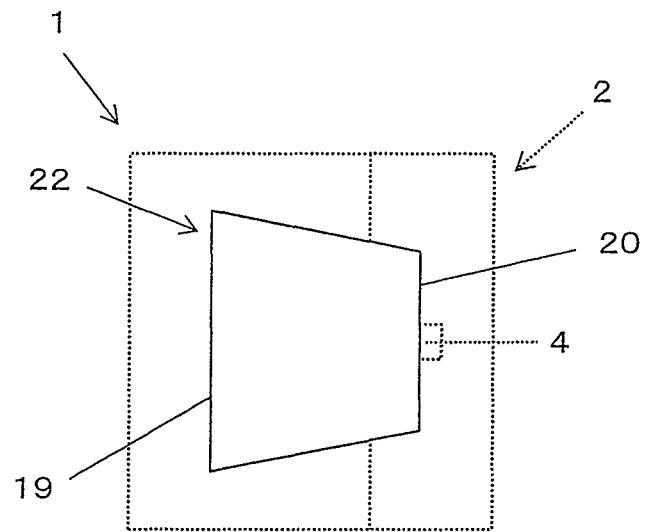
(b)
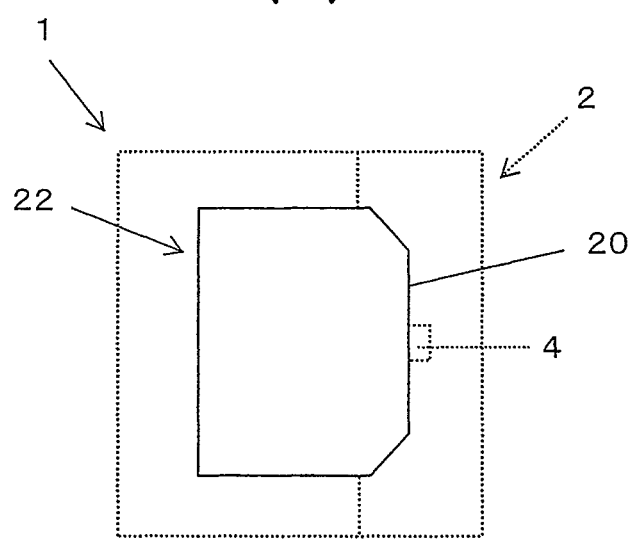

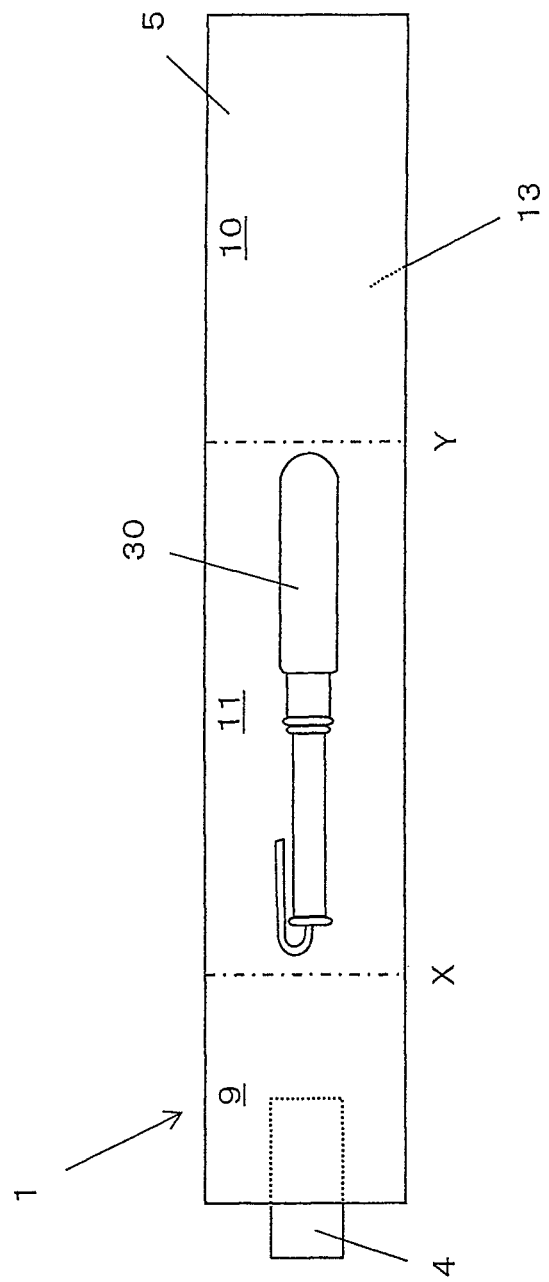

INDIVIDUALLY PACKAGED PRODUCT

TECHNICAL FIELD

The present invention relates to an individually packaged product comprising a first individual package formed by covering an absorbent article with a packaging sheet, and a second individual package.

BACKGROUND ART

Individually packaged products having absorbent articles, such as sanitary napkins, panty liners or paper diapers each wrapped with a single packaging sheet are known in the prior art (see PTL 1 and PTL 2, for example). Individual packaging of the absorbent articles allows each of the absorbent articles to be conveniently and hygienically carried.

Individually packaged sanitary napkins attached with a wipe are also known, as disclosed in PTL 3. Fitting individually packaged sanitary napkins with wipes is convenient as it allows soiled parts to be wiped with a wipe sheet during exchange of a sanitary napkin.

With the individually packaged sanitary napkin illustrated in FIG. 12B and FIG. 15 of PTL 3; however, the inner section and outer section of the release wrapper are anchored only with a tape tab, making it possible for contaminants to infiltrate into gaps between the inner section (for example, 52a in FIG. 15) and outer section (for example, 53a in FIG. 15), creating a hygienic problem.

The individually packaged sanitary napkin illustrated in FIG. 12B and FIG. 15 of PTL 3 is also problematic in that the series of procedures for exchange of the sanitary napkin are difficult to perform.

It is a common procedure that when a sanitary napkin is exchanged, the individually packaged sanitary napkin is opened and the fresh sanitary napkin is separated from the packaging sheet while the used sanitary napkin is adhered to the same packaging sheet, and the used sanitary napkin is wrapped up by the packaging sheet. When a wipe is attached to the individually packaged sanitary napkin, usually the operation is followed by opening of the wipe, removal of the wipe, and use thereof to clean soiled areas.

However, when using the individually packaged sanitary napkin illustrated in FIG. 12B and FIG. 15 of PTL 3, if it is attempted to wrap the used sanitary napkin with the packaging sheet with the unused wipe still attached to the second section, the wipe becomes an interference and the user is thus forced to peel off the wipe from the packaging sheet before wrapping.

With the individually packaged sanitary napkin shown in FIG. 12A of PTL 3, despite the wipe being enclosed by a flap on the "outer section" of the release wrapper, the inner section and outer section of the release wrapper are anchored only by a tape tab. Thus, when using the individually packaged sanitary napkin illustrated in FIG. 12A of PTL 3, contaminants can infiltrate into the gap between the inner section and outer section of the release wrapper and result in hygienic problems, similar to the forms shown in 12B and FIG. 15.

Moreover, with the individually packaged sanitary napkin shown in FIG. 12A of PTL 3, the release wrapper also serves the role of a wipe bag, and therefore when the wipe is a wet type containing a chemical solution or the like, a water-resistant material must be used for the release wrapper and this can potentially increase cost.

CITATION LIST

Patent Literature

[PTL 1] Japanese Unexamined Patent Publication No. 9-10257
[PTL 2] Japanese Unexamined Patent Publication No. 9-10258
[PTL 3] Japanese Unexamined Patent Publication No. 7-506034

SUMMARY OF INVENTION

Technical Problem

It is an object of the present invention to provide an individually packaged product that is resistant to contaminants infiltration and can be hygienically transported.

Solution To Problem

As a result of diligent research directed toward solving the problems described above, the present inventors have completed this invention upon finding that the problems described above can be solved by an individually packaged product comprising a first individual package formed by covering an absorbent article with a packaging sheet, and a second individual package, wherein the packaging sheet has a middle region and a first region and second region located on either side of the middle region, the second region is folded onto the middle region sandwiching the absorbent article therebetween, and the first region is folded onto part of the second region, while the first region is anchored to the outer face of the second region, and the second individual package is situated on the first region and second region and anchored to at least part of the outer face of the first region.

Specifically, the present invention relates to the following aspects.

[Aspect 1]
An individually packaged product comprising a first individual package formed by covering an absorbent article with a packaging sheet, and a second individual package,
wherein the packaging sheet has a middle region and a first region and second region located on either side of the middle region, the second region is folded onto the middle region sandwiching the absorbent article therebetween, and the first region is folded onto part of the second region, while the first region is anchored to the outer face of the second region, and
the second individual package is situated on the first region and second region and anchored to at least part of the outer face of the first region.

[Aspect 2]
The individually packaged product according to aspect 1, wherein the second individual package is further anchored to at least part of the outer face of the second region.

[Aspect 3]
The individually packaged product according to aspect 1 or 2, wherein the first end of the second individual package, located on the anchored end of the first region, is not anchored to the outer face of the first region.

[Aspect 4]
The individually packaged product according to any one of aspects 1 to 3, wherein the second individual package is selected from the group consisting of a packaged wipe, tampon and labial pad.

[Aspect 5]

The individually packaged product according to aspect 4, wherein the second individual package is a packaged wipe, the package of the wipe having an easily openable section that allows the wipe to be easily removed after the used absorbent article has been wrapped with the packaging sheet.

[Aspect 6]

The individually packaged product according to any one of aspects 1 to 5, wherein the material of the packaging sheet is a nonwoven fabric or paper.

[Aspect 7]

The individually packaged product according to any one of aspects 1 to 6, wherein the second individual package has a form indicating the direction for opening the individually packaged product, or has printing indicating the direction for opening the individually packaged product, on the surface of the second individual package.

[Aspect 8]

The individually packaged product according to any one of aspects 1 to 7, wherein the absorbent article is selected from the group consisting of a sanitary napkin, panty liner, and tampon.

[Aspect 9]

The individually packaged product according to any one of aspects 1 to 7, wherein the absorbent article is a paper diaper and the second individual package is a wipe.

Advantageous Effects of Invention

Since the invention according to aspect 1 has the second individual package situated on the first region and second region, contaminants cannot easily infiltrate the space between the free end of the first region and the outer face of the second region, and therefore the individually packaged product can be hygienically carried.

Also, since the invention according to aspect 2 has the second individual package anchored to both at least part of the outer face of the first region and at least part of the outer face of the second region, contaminants infiltrates even less easily than the invention according to aspect 1, and the individually packaged product of the invention can be even more hygienically carried.

Furthermore, since the invention according to aspect 3 has the first end of the second individual package which is not anchored to the outer face of the first region, the second individual package is easily opened from the first end side.

The invention according to aspect 5 has a wipe package with an easily openable section, and therefore the wipe inside it can be easily removed for convenience.

The invention according to aspect 7 has a second individual package with a specified form or printing, and therefore when no gripping tab is present or when gripping tab 4 is hidden by the second individual package, it is possible to easily judge the direction for opening the individually packaged product even when sufficient light is not available, for example.

The invention according to aspect 8 and aspect 9 are convenient, since an article that is used during exchange of the absorbent article or that can be used together with the absorbent article is provided as a set with the absorbent article.

BRIEF DESCRIPTION OF DRAWINGS

FIG. 2(a) is an expanded view of a folded-in-three type first individual package wherein the absorbent article is a sanitary napkin.

FIG. 2(b) is an expanded view of a folded-in-four type first individual package wherein the absorbent article is a sanitary napkin.

FIG. 3 is a cross-sectional view of one aspect of the individually packaged product shown in FIG. 1, along direction 3-3.

FIG. 4(a) is a cross-sectional view showing an example of a method of anchoring the second individual package in an individually packaged product by using a gripping tab, according to some embodiments of the invention.

FIG. 4(b) is a cross-sectional view showing an example of a method of anchoring the second individual package in an individually packaged product without using a gripping tab, according to some embodiments of the invention.

FIG. 8(a) is an illustration showing an example of a second individual package that has a trapezoidal form.

FIG. 8(b) is an illustration showing an example of a second individual package that has a hexagon form.

FIG. 11 is an expanded view of first individual package 2 shown in FIG. 10.

DESCRIPTION OF EMBODIMENTS

The individually packaged product of the invention will now be explained in detail with reference to the accompanying drawings.

Figure 1:
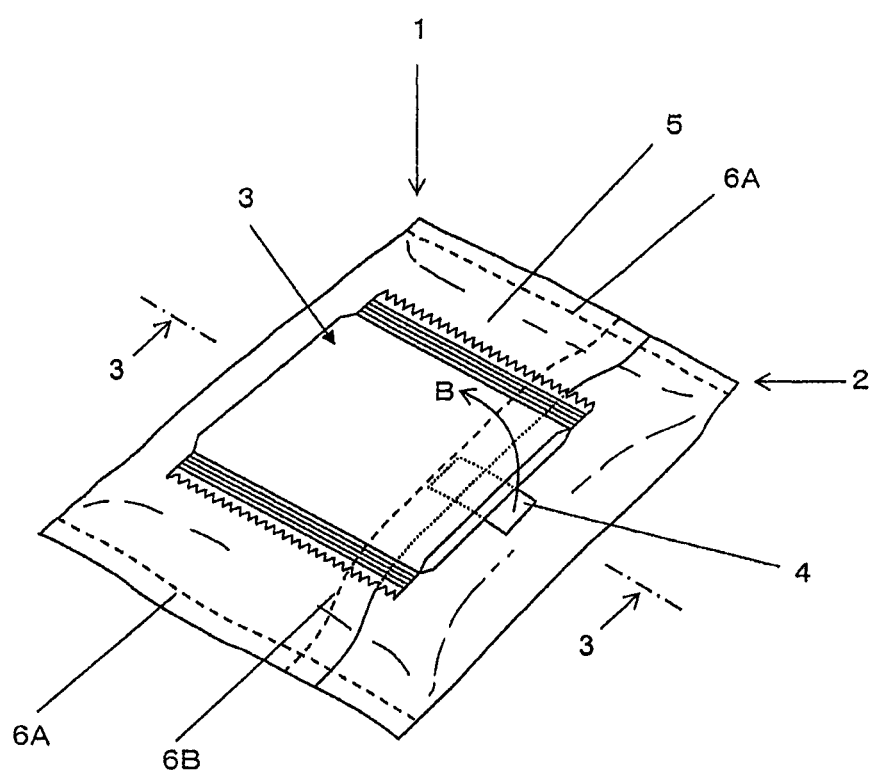
FIG. 1 is a perspective view of one aspect of the individually packaged product of the invention.

FIG. 1 is a perspective view of one aspect of the individually packaged product of the invention. In individually packaged product 1 shown in FIG. 1, packaged wipe 3 as a second individual package is anchored to first individual package 2 that is sealed by gripping tab 4, and seal lines 6A and 6B. During use, the user pulls gripping tab 4 in the direction B to allow the absorbent article to be removed.

Seal lines 6A and 6B are of a type commonly used in the art, and can be formed by using, for example, a heat-welded heat seal, adhesive, hot-melt or the like. The seal lines, including seal line 6B in particular, are provided as desired.

FIG. 2 is an expanded view of a specific aspect of first individual package 2 wherein absorbent article 7 is a sanitary napkin.

FIG. 2(a) shows a folded-in-three type first individual package 2. First individual package 2 in FIG. 2(a) is formed from absorbent article 7 and packaging sheet 5, the back side of absorbent article 7 being covered by packaging sheet 5 and anchored to packaging sheet 5.

The means for anchoring absorbent article 7 to packaging sheet 5 may be, for example, a pressure-sensitive adhesive commonly used in the art.

As used herein, the "back side" of the absorbent article is the side facing clothing during use. As used herein, the "front side" of the absorbent article is the side facing the user during use.

Packaging sheet 5 in FIG. 2(a) comprises middle region 11, and first region 9 and second region 10 located on either side of middle region 11. When in individually packaged state thereof, second region 10 is folded along crease line Y together with absorbent article 7, over onto middle region 11, so that the front side of absorbent article 8 faces inward, and then first region 9 is folded along crease line X over onto part of second region 10, and first region 9 is anchored to outer face of second region 13 by gripping tab 4.

As used herein, the "outer faces" of the first region and second region are the sides facing outward when in the individually packaged state. The "inner faces" of the first region and second region are the sides facing inward when in the individually packaged state.

FIG. 2(b) shows a folded-in-four type first individual package 2. First individual package 2 in FIG. 2(b), similar to that of FIG. 2(a), is formed from absorbent article 7 and packaging sheet 5, the back side of absorbent article 7 being covered by packaging sheet 5 and anchored to packaging sheet 5.

Packaging sheet 5 in FIG. 2(b) comprises middle region 11, and first region 9 and second region 10 located on either side of middle region 11. Second region 10 further comprises section of second region 15 that includes free end of second region 14D, and remaining section of second region 16 located between section of second region 15 and middle region 11.

When in an individually packaged state thereof, section of second region 15 is folded along crease line Z together with absorbent article 7, over onto remaining section of second region 16, so that front side of absorbent article 8 faces inward, while also being folded along crease line Y over onto middle region 11, and then first region 9 is folded along crease line X over onto part of second region 10 (more specifically, remaining section of second region 16), and first region 9 is anchored to outer face of second region 13 (more specifically, remaining section of second region 16) by gripping tab 4.

Sections 14A, 14B and 14C are the free end of the first region, the anchored end of the first region and the anchored end of the second region, respectively, and 17A and 17B are the side edges of the packaging sheet.

As used herein, "anchored end" refers to the end of the first region or second region adjacent to the middle region, and "free end" refers to the end of the first region or second region opposite the middle region side.

When the back side of absorbent article 7 is anchored to three regions of packaging sheet 5, middle region 11, first region 9 and second region 10, with a pressure-sensitive adhesive or the like, as shown in FIG. 2(a), absorbent article 7 is generally folded in three, together with packaging sheet 5; however when the back side of absorbent article 7 is anchored to two regions of packaging sheet 5, i.e., middle region 11 and second region 10, for example, absorbent article 7 may be folded in two, together with packaging sheet 5.

Also, when the back side of absorbent article 7 is anchored to middle region 11, first region 9, section of second region 15 and remaining section of second region 16 of packaging sheet 5, with a pressure-sensitive adhesive or the like, as shown in FIG. 2(b), absorbent article 7 is generally folded in four, together with packaging sheet 5; however when the back side of absorbent article 7 is anchored to middle region 11, section of second region 15 and remaining section of second region 16 of packaging sheet 5, or when the back side of absorbent article 7 is anchored to middle region 11, first region 9 and the remaining section 16 of the second region of packaging sheet 5, absorbent article 7 may be folded in three, together with packaging sheet 5.

Even when absorbent article 7 is a panty liner as described below, the panty liner may be individually packaged as shown in FIG. 2(a) and FIG. 2(b), similar to a sanitary napkin.

On the other hand, when the back side of absorbent article 7 is not anchored to packaging sheet 5, absorbent article 7 can be (i) individually packaged being folded over once or several times with the packaging sheet, (ii) individually packaged by packaging sheet 5 after having been folded over once or several times separately from the packaging sheet, or (iii) individually packaged in packaging sheet 5 without being folded over.

As absorbent articles according to aspects (i) and (ii), there may be mentioned sanitary napkins, panty liners and the below-mentioned paper diapers, having the adhesive section of the back side covered with a release sheet, and as absorbent articles according to aspect (iii), there may be mentioned tampons.

The absorbent articles used in the invention are not particularly restricted so long as they can be sold in a form individually packaged with a packaging sheet, and as examples, there may be mentioned sanitary napkins and panty liners, as well as paper diapers, such as tape-type paper diapers and pants-type paper diapers.

The packaging sheet used in the invention is not particularly restricted so long as it can be used in the art for individual packaging, and there may be mentioned nonwoven fabrics, films, sheets and laminates thereof. When the absorbent article is a sanitary napkin, panty liner or the like, a packaging sheet, release-treated with silicone, for example, may be used in order to protect the adhesive sections that serve to attach the absorbent article to shorts.

As first individual packages used in the invention, there may be mentioned sanitary napkins, panty liners, paper diapers and tampons, each packaged with the aforementioned packaging sheet.

First individual packages wherein the absorbent article is a sanitary napkin may be the sanitary napkin packages described in PTL 1 and PTL 2, Japanese Unexamined Patent Publication No. 2003-175990 and Japanese Unexamined Patent Publication No. 2006-280522, used without modification.

First individual packages wherein the absorbent article is a tampon may be the individual package for a sanitary tampon described in Japanese Unexamined Patent Publication No. 2008-259583, used without modification.

FIG. 3 is a cross-sectional view of one aspect of the individually packaged product shown in FIG. 1, along direction 3-3, wherein absorbent article 7 is folded in three, together with packaging sheet 5. In FIG. 3, first region 9 is folded onto outer face of second region 13 together with absorbent article 7, while first region 9 is anchored to outer face of second region 13 by gripping tab 4. Packaged wipe 3, as the second individual package, is anchored by adhesive 18 onto first region 9.

Packaged wipe 3 comprises first end 19 on anchored end of first region 14B side, and second end 20 on free end of first region 14A side.

In individually packaged product 1 in FIG. 3, packaged wipe 3 does not cover the entire gripping tab 4; however the edge of gripping tab 4B is provided nearer anchored end of second region 14C than second end 20, allowing the user to directly pull edge of gripping tab 4B. During use, therefore, the user grips gripping tab 4 and pulls it up, to allow absorbent article 7 to be removed.

The user can alternatively grip the section near second end 20 instead of gripping tab 4 and pull it up to allow absorbent article 7 to be removed. If second end 20 is to be gripped and pulled up, adhesive 18 is preferably near second end 20. This will further facilitate opening. Adhesive 18 may also be provided on part of gripping tab 4.

In packaged wipe 3 in FIG. 3, first end 19 and the area near second end 20 are not anchored to first individual package 2, and only center region 21 of packaged wipe 3 is anchored to first individual package 2 by adhesive 18.

As used herein, the term "pressure sensitive adhesion" refers to temporary anchoring. The term "adhesion" refers to both permanent attachment and temporary attachment.

Also as used herein, "pressure-sensitive adhesive" refers to an agent used for temporary attachment, and "adhesive" refers to both an agent used for permanent attachment and an agent used for temporary attachment.

Adhesive 18 may be an adhesive commonly used in the art, such as a hot-melt adhesive, among which polyolefin (such as polyethylene and polypropylene)-based hot-melt adhesives, ethylene/vinyl acetate copolymer-based hot-melt adhesives, synthetic rubbers (such as styrene-based polymer, butadiene-based polymer and isoprene-based polymer)-based hot-melt adhesives and acrylic resin-based pressure-sensitive adhesives are examples.

The width in the direction of side edges of the second individual package 25A and 25B, in the region in which adhesive 18 is applied, is preferably as long as possible from the viewpoint of preventing infiltration of contaminants. Bonding up to the edge of the second individual package; however, may interfere with opening of the second individual package itself. A non-bonded section is therefore preferably left near side edges of the second individual package 25A and 25B.

Figure 9:
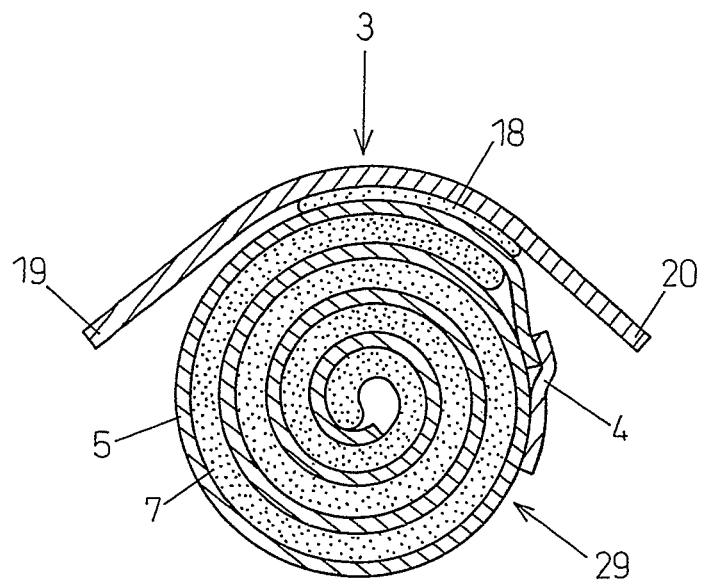
FIG. 9 is an illustration schematically showing the cross-section of individually packaged product 1 according to the invention just before opening of packaged wipe 3, during exchange of an absorbent article.

When absorbent article 7 is a sanitary napkin or panty liner, the length in the direction of first end 19 and second end 20, in the region in which adhesive 18 is applied, is preferably no greater than 4 cm and more preferably no greater than 3 cm. This is because when the used absorbent article is wrapped with the packaging sheet, the diameter of the cross-section of the used absorbent article wrapped by packaging sheet 29, as shown in FIG. 9 explained below, will generally be about 3-4 cm.

FIG. 4 is a cross-sectional view showing an example of a variation on the method of anchoring the second individual package in an individually packaged product according to the invention. In individually packaged product 1 of FIG. 4(a), although first region 9 is anchored to outer face of second region 13, the entire gripping tab 4 is hidden by second individual package 22. The user can therefore grip the section near second end 20 instead of gripping tab 4 and pull it up to allow the contained absorbent article 7 to be removed. In the case of FIG. 4(a), adhesive 18 is preferably provided nearer second end 20 for easier opening. Adhesive 18 may also be provided on part of gripping tab 4.

In individually packaged product 1 in FIG. 4(b), no gripping tab 4 is provided and second individual package 22 is anchored to first region 9 and outer face of second region 13 by adhesive 18. The aspect shown in FIG. 4(b) is economically advantageous since gripping tab 4 can be omitted.

In the aspect shown in FIG. 4(b), incidentally, adhesive 18 is preferably a pressure-sensitive adhesive for temporary anchoring. This is because at least part of adhesive 18 must be peeled during use.

The aspect shown in FIG. 4(b) is preferred because it has the second individual package covering first region 9 and outer face of second region 13, and it anchors both first region 9 and outer face of second region 13 with an adhesive, and therefore no or very little gap is formed between first region 9 and outer face of second region 13 and infiltration of contaminants is inhibited. Also, since the aspect shown in FIG. 4(b) is resistant to infiltration of contaminants in the gap between first region 9 and outer face of second region 13, it is possible to omit the seal line shown as 6B in FIG. 1 and thus provide an economical advantage.

As used herein, the second individual package may be one used for exchange of an absorbent article, or one used in combination with an absorbent article. As examples of articles to be used for exchange of an absorbent article, there may be mentioned packaged wipes, and as examples of articles to be used in combination with absorbent articles, there may be mentioned packaged tampons and labial pads.

As used herein, the amount included in the "individual package" of the first individual package and second individual package, is an amount for one usage, and in the case of a sanitary napkin, panty liner, tampon or labial pad, for example, it will usually consist of one item or sheet, while in the case of a packaged wipe it may include one or several sheets, depending on for example, the size thereof.

Figure 5:
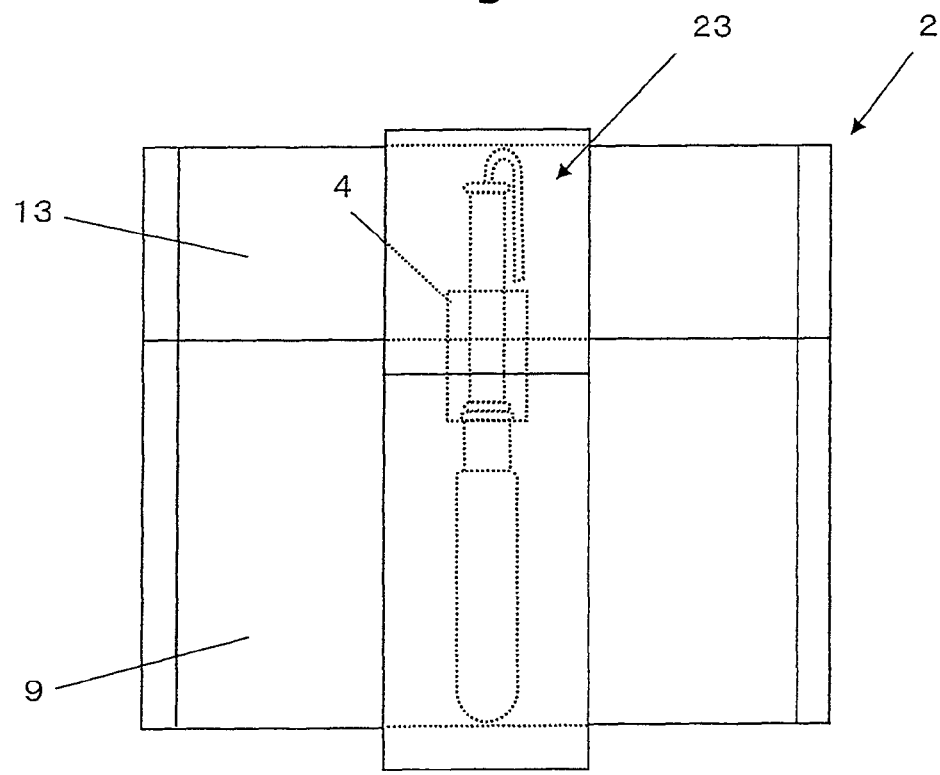
FIG. 5 is a front view of an individually packaged product of the invention wherein the second individual package is a packaged tampon.

FIG. 5 is a front view of an individually packaged product wherein the second individual package is packaged tampon 23. In FIG. 5, first region 9 and outer face of second region 13 of first individual package 2 are anchored by gripping tab 4; however, first region 9 and outer face of second region 13 of first individual package 2 may be anchored by packaged tampon 23 itself instead of gripping tab 4, as in FIG. 4(b).

Packaged tampon 23 as the second individual package may also be anchored to first individual package 2 in a rotation of 90°, 180° or 270° in the clockwise direction on the basis of packaged tampon 23 of FIG. 5.

Such a packaged tampon may be the individual package for a sanitary tampon described in Japanese Unexamined Patent Publication No. 2008-259583, used without modification.

Figure 6:
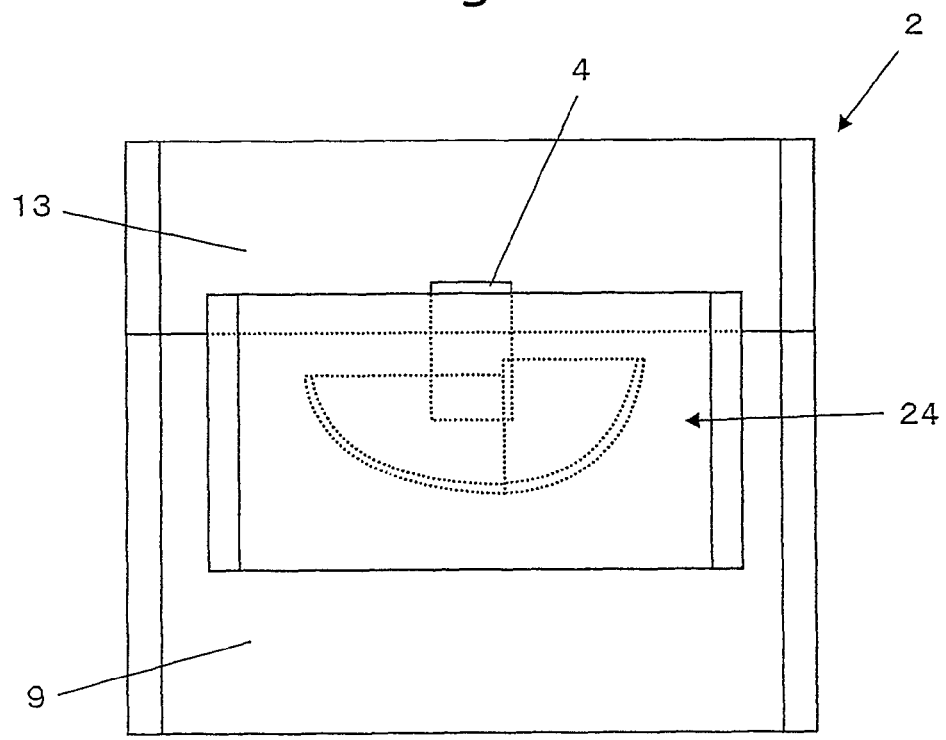
FIG. 6 is a front view of an individually packaged product of the invention wherein the second individual package is a packaged labial pad.

FIG. 6 is a front view of an individually packaged product wherein the second individual package is packaged labial pad 24. In FIG. 6, first region 9 and outer face of second region 13 of first individual package 2 are anchored by gripping tab 4; however, first region 9 and outer face of second region 13 of first individual package 2 may be anchored by packaged labial pad 24 itself instead of gripping tab 4, as in FIG. 4(b).

Packaged labial pad 24 as the second individual package may also be anchored to first individual package 2 in a rotation of 90°, 180° or 270° in the clockwise direction on the basis of packaged labial pad 24 of FIG. 6.

Such a packaged labial pad may be the individually packaged labial pad described in International Patent Publication No. WO2002/094149, used without modification.

Figure 7:
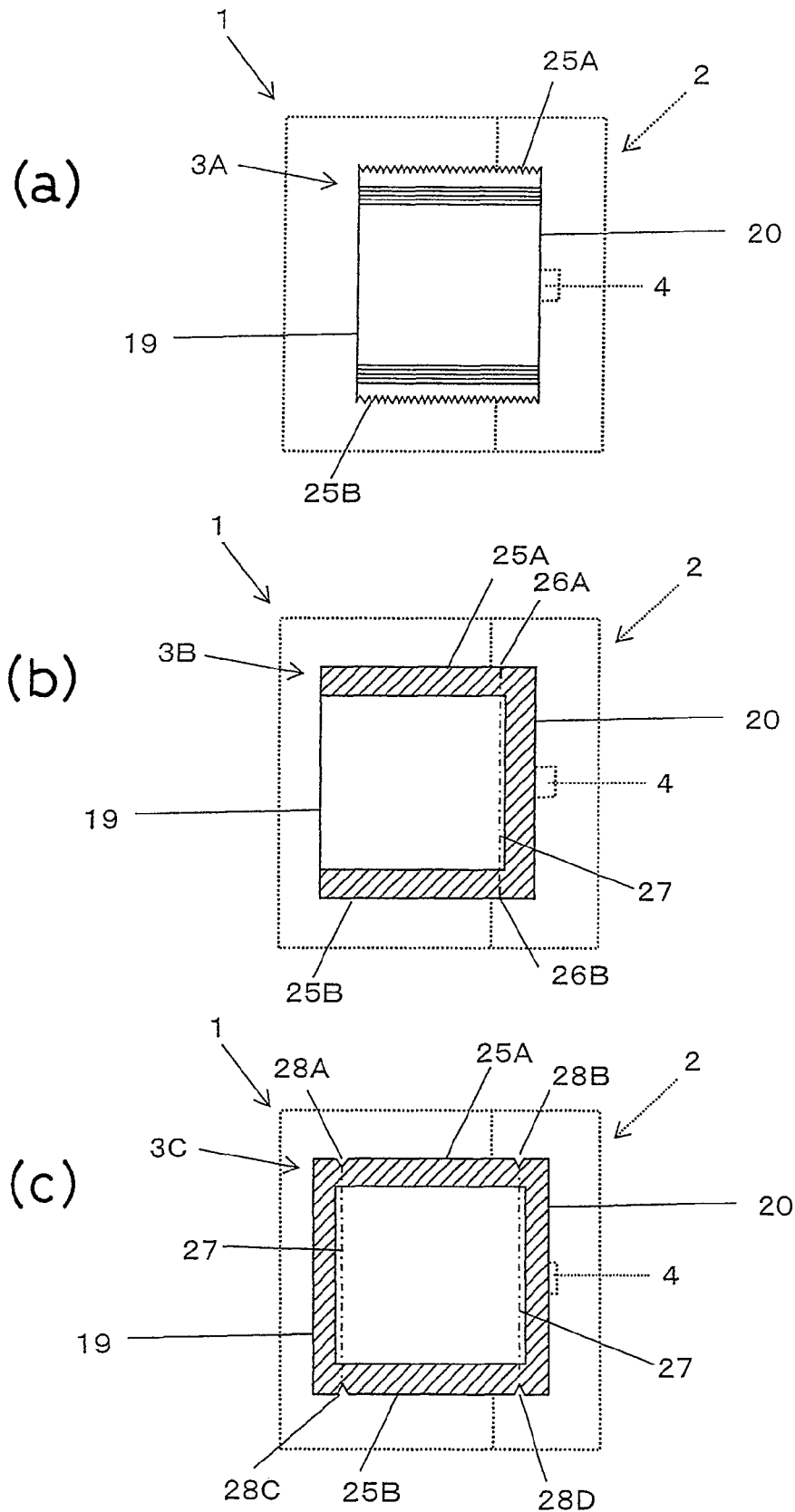
FIG. 7(a) is a front view showing an example of the packaging of a packaged wipe that uses a pillow package.
FIG. 7(b) is a front view showing an example of the packaging of a packaged wipe that uses a three-way seal package.
FIG. 7(c) is a front view showing an example of the packaging of a packaged wipe that uses a four-way seal package.

FIG. 7 is an illustration shown a variation of packaging, wherein the second individual package is packaged wipe 3. In FIG. 7, first individual package 2 is indicated by a dotted line to facilitate understanding of the positional relationship with the first individual package. During opening, gripping tab 4 or wipe is pulled upward toward the left to allow individually packaged product 1 to be opened.

FIG. 7(a) shows wipe with pillow package 3A (hereinafter referred to simply as "wipe 3A"). FIG. 7(b) shows wipe with three-way seal package 3B (hereinafter referred to simply as "wipe 3B"). FIG. 7(c) shows wipe with four-way seal package 3C (hereinafter referred to simply as "wipe 3C").

As used herein, "pillow package" is a package produced by rolling the packaging material into a circular cylinder and sealing both edges. A "three-way seal package" is a package produced by folding the packaging material in two and sealing the three sides other than the folded-in-two section. A "four-way seal package" is a package produced by stacking two packaging materials and sealing the four sides.

These wipes 3A, 3B and 3C preferably have easily openable sections to allow the wipes to be easily removed after the used absorbent article has been wrapped with the packaging sheet.

FIG. 9 is an illustration schematically showing the cross-section of individually packaged product 1 according to the invention just before opening of packaged wipe 3, during exchange of an absorbent article. The following is a common procedure for exchange of an absorbent article. First, individually packaged product 1 of the invention is opened, and the fresh absorbent article 7 is released from packaging sheet 5. Next, the used absorbent article is wrapped with packaging sheet 5 to create used absorbent article wrapped by the packaging sheet 29. Packaged wipe 3 anchored to used absorbent article wrapped by packaging sheet 29 is then opened and the soiled areas are cleaned. The fresh absorbent article is then attached to the shorts.

Since the individually packaged product is usually in the state shown in FIG. 9 just prior to removal of the wipe from packaged wipe 3, as mentioned above, it is considered convenient to provide an easily openable section to allow opening of packaged wipe 3 along first end 19 and/or second end 20 of packaged wipe 3.

In FIG. 7(a), a jagged section with a plurality of notches is attached to provide easily openable sections on side edges of second individual package 25A and 25B of second individual package with a pillow package. The package may be opened along first end 19 and/or second end 20 from the jagged sections to allow easy removal of the wipe. The jagged sections may be on either or both of side edges of packaging sheet 25A and 25B.

As used herein, "side edges of second individual package" means the edges of the second individual package that are on the same sides as the side edges of the first individual package after bonding to the first individual package.

In the three-way seal package in FIG. 7(b), a total of 3 locations, second end 20 and side edges of second individual package 25A and 25B, are sealed. Slit sections 26A and 26B are provided as easily openable sections near second end 20 within side edges of second individual package 25A and 25B. Guide line 27 is provided as desired between slit sections 26A and 26B. Opening is accomplished along guide line 27 from slit section 26A or 26B, allowing the wipe to be removed. Guide line 27 may be a printed dotted line, for example.

The diagonal sections in FIG. 7(b) represent the sealed sections.

In the four-way seal package in FIG. 7(c), a total of 4 locations, first end 19, second end 20 and side edges of second individual package 25A and 25B, are sealed. On side edge of second individual package 25A, there are provided notch 28A near first end 19 and notch 28B near second end 20, as easily openable sections, while on the side edge of second individual package 25B, there are provided notch 28C near first end 19 and notch 28D near second end 20. Guide line 27 is provided as desired between notch 28A and notch 28C, and between notch 28B and notch 28D. Opening is accomplished along first end 19 or second end 20 from any of the notches, to allow the wipe to be removed.

The diagonal sections in FIG. 7(c) represent the sealed sections.

The packaging of packaged wipe 3 may be the aforementioned pillow package, three-way seal package, four-way seal package or the like, and such packages may include a combination of easily openable sections composed of the jagged sections, slit sections and notches, and a guide line as desired, as described above. When the package is a three-way seal package or four-way seal package, the easily openable section described above includes an easily openable section which is a cohesive release type opened by being turned up while inducing cohesive fracture of a layer, or a delamination type opened by being turned up while inducing delamination between two layers, in a packaging composed of multiple layers.

The wipe used in the invention is not particularly restricted and may be suitably used, so long as it is commonly used as a wipe in the art. The wipe used in the invention may be a dry type or wet type. The material of the wipe may be a nonwoven fabric or woven fabric composed of hydrophilic fiber or a mixture of hydrophilic fiber and non-hydrophilic fiber. As hydrophilic fibers, there may be mentioned regeneration cellulose fiber, such as rayon or natural fiber, such as cotton or pulp, and as non-hydrophilic fiber, there may be mentioned polyester or polypropylene.

Considering that the wipe is to be flushed from the toilet after use, it preferably has hydrolyzability, and is most preferably a nonwoven fabric with hydrolyzability.

A binder may be added to the wipe to further increase the wet strength. As examples of binders, there may be mentioned alkylcelluloses, such as carboxymethylcellulose, methylcellulose, ethylcellulose and benzylcellulose, as well as polyvinyl alcohol, modified polyvinyl alcohols containing prescribed amounts of sulfonic acid or carboxyl groups, and polyamide-epichlorhydrin.

When the wipe is a wet type, and the material is composed of a mixture of hydrophilic fiber and non-hydrophilic fiber, the proportion of hydrophilic fiber is preferably at least 40 mass % based on the total fiber mass. This will allow the wipe to retain a chemical solution, as explained below.

The wipe preferably has a basis weight of 20-100 $g/m^2$ from the viewpoint of ease of use.

When the wipe is a wet type, the wipe may contain a chemical solution at 100-500 mass % with respect to the mass of the wipe. Such a chemical solution may be a mixture of a minimal necessary amount of an antiseptic agent in purified water. The chemical solution may also contain, as necessary, various additives used in the art, such as one or more surfactants, moisturizing agents, refreshers, emollients, pH adjustors, perfumes, antioxidants, chelating agents, plant extracts, anti-browning agents, flash reducing agents, skin activators, astringents and tactile improvers.

The material of the wipe package is not particularly restricted, and can be one that is one commonly used for packaging in the art, such as polyester, polypropylene or polyethylene terephthalate films, aluminum foil, paper or the like, either as a single layer or multiple layers. In a three-way seal package or four-way seal package described above, the seal sections may be formed by melt bonding of the film sections with heat or ultrasonic waves, or by using a hot-melt adhesive or adhesive for bonding.

Second individual package 22 used in the invention may also have a modification to form thereof (for example, a change in the length of first end 19 with respect to the length of second end 20) or printing on the front side of second individual package 22, to clearly indicate the direction of opening of the individually packaged product of the invention. FIG. 8 is an illustration showing an example of a variation on the form of second individual package 22. In FIG. 9, first individual package 2 is indicated by a dotted line, as the position of second individual package 22 in individually packaged product 1. During opening, gripping tab 4 or second individual package 22 is pulled upward toward the left to open individually packaged product 1.

In FIG. 8(a), second individual package 22 has a trapezoidal form with second end 20 as the top base and first end 19 as the bottom base. In FIG. 8(b), the form is a hexagon obtained by eliminating two vertices from second end 20 side.

By employing such a form it is possible for the user to easily determine the direction of opening even when no gripping tab 4 is provided or when gripping tab 4 is hidden by second individual package 22. The direction of opening of the individually packaged product can also be easily judged in locations where the light quantity is inadequate.

Printed characters indicating the direction of opening may also be provided on the surface of second individual package 22.

Figure 10:
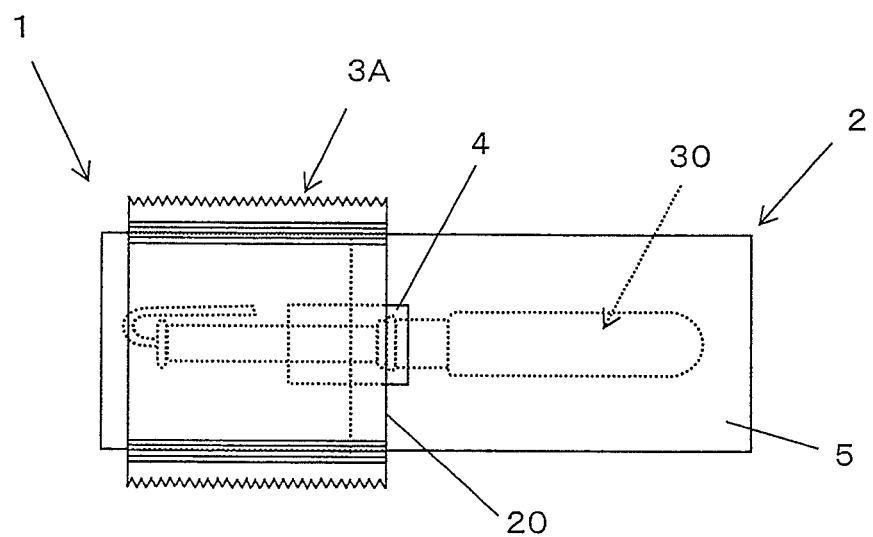
FIG. 10 is a front view of individually packaged product 1 wherein the absorbent article is a tampon and the second individual package is a wipe with a pillow-type package.

FIG. 10 is a front view of individually packaged product 1 wherein absorbent article 7 is tampon 30 and second individual package 22 is wipe 3A with a pillow-type package.

During use, for example, the user can hold gripping tab 4 or second end 20 of wipe 3A and open toward the left first individual package 2, remove tampon 30 inside, place the used tampon in packaging sheet 5, remove the wipe from wipe 3A, clean the soiled areas, and insert the fresh tampon 30.

As the first individual package wherein the absorbent article is a tampon, there may be used the individual package for a sanitary tampon described in Japanese Unexamined Patent Publication No. 2008-259583.

FIG. 11 is an expanded view of first individual package 2 shown in FIG. 10.

When in individually packaged state thereof, second region 10 is folded along crease line Y over onto middle region 11 to sandwich tampon 30, and then first region 9 is folded along crease line X over onto part of second region 10, and first region 9 is anchored to outer face of second region 13 by gripping tab 4.

Although gripping tab 4 is shown in FIGS. 10 and 11, first region 9 and outer face of second region 13 of the packaging sheet may be anchored by the second individual package, such as wipe 3A, instead of by gripping tab 4, as in FIG. 4(b).

References Signs List
1 Individually packaged product
2 First individual package
3 Packaged wipe
3A Wipe with pillow package
3B Wipe with three-way seal package
3C Wipe with four-way seal package
4 Gripping tab
4B Edge of gripping tab
5 Packaging sheet
6A, 6B Seal lines
7 Absorbent article
8 Front side of absorbent article
9 First region
10 Second region
11 Middle region
12 Outer face of first region
13 Outer face of second region
14A Free end of first region
14B Anchored end of first region
14C Anchored end of second region
14D Free end of second region
15 Section of second region
16 Remaining section of second region
17A, 17B Side edges of packaging sheet
18 Adhesive
19 First end
20 Second end
21 Center region
22 Second individual package
23 Packaged tampon
24 Packaged labial pad
25A, 25B Side edges of second individual package
26A, 26B Slit sections
27 Guide line
28A, 28B, 28C, 28D Notches
29 Used absorbent article wrapped by packaging sheet
30 Tampon
X, Y, Z Crease lines

The invention claimed is:

1. An individually packaged product comprising a first individual package formed by covering an absorbent article with a packaging sheet, and a second individual package,
wherein the packaging sheet has a middle region and a first region and second region located on either side of the middle region, the second region is folded onto the middle region sandwiching the absorbent article therebetween, and the first region is folded onto part of the second region, while the first region is anchored to the outer face of the second region, and
the second individual package is anchored to at least part of the outer face of the first region and at least part of the outer face of the second region, and extends to conceal at least a portion of the outer face of the second region where the first region is anchored to the second region.

2. The individually packaged product according to claim 1, wherein the first end of the second individual package, located on the anchored end of the first region, is not anchored to the outer face of the first region.

3. The individually packaged product according to claim 1, wherein the second individual package is selected from the group consisting of a packaged wipe, tampon and labial pad.

4. The individually packaged product according to claim 3, wherein the second individual package is a packaged wipe, the package of the wipe has an easily openable section that allows the wipe to be easily removed after the used absorbent article has been wrapped with the packaging sheet.

5. The individually packaged product according to claim 1, wherein the material of the packaging sheet is a nonwoven fabric or paper.

6. The individually packaged product according to claim 1, wherein the second individual package has a form indicating the direction for opening the individually packaged product, or has printing indicating the direction for opening the individually packaged product, on the surface of the second individual package.

7. The individually packaged product according to claim 1, wherein the absorbent article is selected from the group consisting of a sanitary napkin, panty liner and tampon.

8. The individually packaged product according to claim 1, wherein the absorbent article is a paper diaper and the second individual package is a wipe.

* * * * *